United States Patent
Rogers et al.

[11] Patent Number: 5,133,707
[45] Date of Patent: Jul. 28, 1992

[54] TRANSPARENT INDICIA EMBOSSED FILM

[75] Inventors: Wallace S. Rogers, St. Anthony; Alan J. Sipinen, Hugo, both of Minn.

[73] Assignee: Minnesota Mining and Manufacturing Company, St. Paul, Minn.

[21] Appl. No.: 558,614

[22] Filed: Jul. 26, 1990

[51] Int. Cl.⁵ ............................................. A61F 13/15
[52] U.S. Cl. ................................. 604/389; 604/385.1; 40/616; 428/29
[58] Field of Search ..................... 128/158, 156; 604/385.1, 389, 390, 386, 387, 376, 372, 380, 382; 40/616; 428/29

[56] References Cited

U.S. PATENT DOCUMENTS

| | | | |
|---|---|---|---|
| 2,532,011 | 11/1950 | Dahlquist et al. | 154/53.5 |
| 3,053,252 | 9/1962 | Wolf | 604/385.1 |
| 3,248,858 | 4/1966 | Stenvall | 128/156 |
| 3,457,919 | 7/1969 | Harbard | 128/156 |
| 3,542,134 | 11/1970 | Such et al. | 128/156 |
| 3,932,328 | 1/1976 | Korpman | 260/27 BB |
| 3,954,692 | 5/1976 | Downey | 260/33.6 |
| 3,961,112 | 6/1976 | Genevitz et al. | 40/616 |
| 4,047,529 | 9/1977 | Karami | 128/287 |
| 4,135,023 | 1/1979 | Lloyd et al. | 128/156 |
| 4,227,530 | 10/1980 | Schatz | 128/287 |
| 4,249,534 | 2/1981 | Polansky et al. | 604/385.1 |
| 4,334,530 | 6/1982 | Hassell | 128/156 |
| 4,389,212 | 6/1983 | Tritsch | 604/389 |
| 4,581,087 | 4/1986 | Johnson | 128/156 |
| 4,662,875 | 5/1987 | Hirotsu et al. | 604/389 |
| 4,778,701 | 10/1988 | Pape et al. | 428/40 |

Primary Examiner—Randall L. Green
Assistant Examiner—K. M. Reichle
Attorney, Agent, or Firm—Gary L. Griswold; Roger R. Tamte; William J. Bond

[57] ABSTRACT

A composite adhesive fastening tape and tape system for interconnecting printed surfaces, which includes a transparent main film portion with an embossed surface defined logo or symbol or the like and coated on one surface with an adhesive, in the tape system is included a target film portion, which target film portion is optionally decorated by colored numbers, letters, patterns, shapes or figures.

17 Claims, 1 Drawing Sheet

TRANSPARENT INDICIA EMBOSSED FILM

BACKGROUND AND FIELD OF THE INVENTION

The invention concerns an adhesive fastening tape and system and, particularly, an improved embossed fastening tape for use in a diaper having a printed front portion.

Disposable diapers generally comprise an absorbent core layer sandwiched between a liquid permeable user contacting sheet ("topsheet") and a liquid impermeable outer sheet ("backsheet"). The diaper, or other like absorbent articles are flat or folded when sold and typically fitted to the individual user with an adjustable closure system. The most common fastening means used in these closure systems are adhesive tape fasteners (see, e.g., U.S. Pat. Nos. 4,778,701, (Pape et al.), 4,227,530 (Schatz) and 4,047,529, (Karami) and U.S. Pat. No. 4,389,212 (Tritsch), who discloses a tape having an elastic portion). These tapes will conventionally be formed of a thermoplastic backing having an adhesive layer on one side. The tapes currently used are generally opaque or translucent and permanently attached at one side of the diaper. A free end will be temporarily attached, ready for user placement. The free end of the tape will typically be temporarily placed on a release tape on the topsheet side of the diaper. The fastening tapes are located on each side of the diaper and when used the free end is attached to a frontal tape or reinforced section on the diaper backsheet side.

The placement of the free ends of fastening tapes on the diaper backsheet defines the shape of the diaper, particularly the waist and leg openings size and shape. The proper placement of the fastening tape free end and its criticality is discussed in U.S. Pat. No. 4,662,875 (Hirotsu et al). Hirotsu et al. proposed placing indicia on the front of the diaper backsheet. The indicia allegedly could be used by the individual fitting the diaper to properly align and place the free ends of fastening tapes on the diaper backsheet. The use of such indicia has become increasing popular due to both its above functional purpose, and for aesthetic reasons. In order to prevent obfuscation of these indicia (often quite colorful) by the fastening tape itself there has been some use of clear fastening tapes. However, in the past fastening tapes themselves were provided decorative finishes and/or indicia such as logos, although this practice interferes with the objective of preventing obfuscation of indicia on the diaper backsheet.

SUMMARY OF THE INVENTION

According to the present invention, a decorative adhesive fastening tape is provided for a diaper or like articles. The novel fastening tape is embossed to create distinct indicia, which are visible at least on the free end when held by the user prior to attachment. However, once applied to the diaper, the embossed created indicia will essentially become imperceivable and allow viewing of any indicia on the landing area where the tape free end is attached. Additionally, the release coated surface, to which the embossed fastening tape free end is adhered prior to use, can also permit display of the embossed indicia on the fastening tape.

DESCRIPTION OF THE INVENTION

Figure 1:
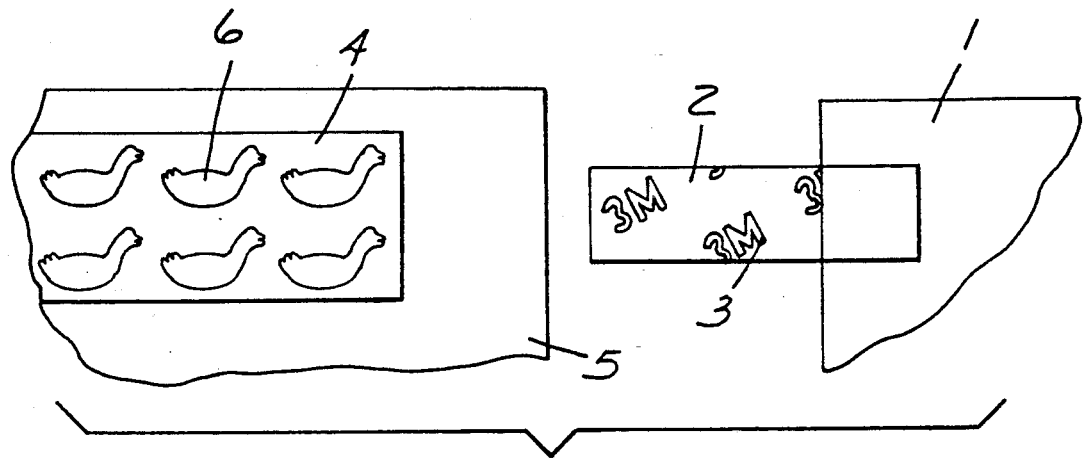
FIG. 1 is a side view of a corner of a diaper and its backsheet sections showing a tape landing area with decorative figures thereon and a transparent fastening tape portion with a "3M" logo embossed thereon.
Figure 2:
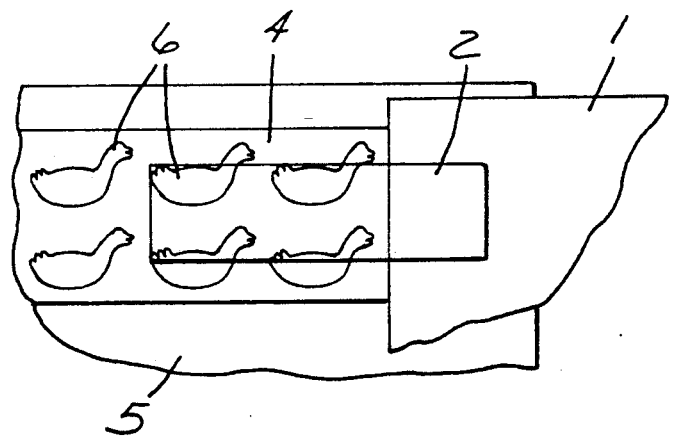
FIG. 2 is a side view of the two sections of FIG. 1 where the fastening tape is adhered to the target area.

As shown in FIG. 1, the present invention provides a novel diaper fastening tape 2, which is embossed with, for example, logo 3, which is at least visible to the user when the diaper fastening tape free end is removed from the release tape (not shown) until the tape is applied to a landing area 4 on the diaper 1. More specifically, the present invention relates to a novel adhesive tape system for interconnecting diaper surfaces which comprises a transparent fastening tape having at least one portion which has been embossed to provide distinctive indicia, for example, letters and/or numbers and/or shapes and/or patterns and/or figures as shown in FIG. 1. Additionally, the system will comprise a landing area portion 4 which may be a diaper backsheet or a frontal reinforcing tape 5. The backsheet or the frontal tape at the landing area 4 can be decorated by colored numbers, letters or FIGS. 6. These colored numbers, letters, figures and the like 6 remain visible when the transparent embossed fastening tape is applied to the landing area 4 as shown in FIG. 2.

Indicia are used extensively on the diaper frontal or fastening tape landing area, which is the area where the fastening tape free end embossed portion is most likely and desirably attached. These indicia are used for decorative and functional reasons as explained, for example, in U.S. Pat. No. 4,662,875, the substance of which is incorporated herein by reference. Such indicia aid the individual fitting the article to the user in promptly locating a desirable affixation point for the fastening tape free end to provide for a proper fit. The indicia guide the applicators eye so that once one fastening tape free end is applied, the second fastening tape free end can be applied to a corresponding spot on the other side of the diaper. In a desired embodiment, the free end of the adhesive fastening tape would be removable to allow for fitting adjustments and diaper checking. The embossed fastening tape of the invention is ideally suited for use in a diaper as described above as it permits viewing of the indicia under the fastening tape. With conventional opaque fastening tapes, the indicia on the landing area would be obscured by the tape making proper fitting, using these indicia as guides, more difficult as well as obscuring any ornamental effect provided by the indicia on the diaper.

The components of the embossed fastening tape of the invention are generally not material dependent except to the extent that transparency is required. Film used to manufacture the fastening tape backing can be any of the films generally used for tape backings, for example, material which can be cast or extruded such as polyethylene, polypropylene, polyethylene copolymers, polypropylene copolymers, polyethylene terephthalate, cellulose acetate and the like. It is highly desirable that the film material be castable or extrudable since the preferred manufacturing methods currently available for producing embossed films are those wherein a molten polymer is cast onto or from a surface having engraved, molded, etched, sand blasted or otherwise relieved with differently surfaced regions for the indicia and the background such as a roll. This surface imparts the desired embossed defined indicium (e.g., a logo) to the film. Alternatively, the embossed defined indicia may be imparted to a film by post-formation heating a cast, or otherwise-formed, film sufficiently to soften it, and contacting the film with a surface as described above to allow embossing, while avoiding overheating which could melt the film.

It is necessary that the embossed films and articles made therefrom be relatively transparent, i.e., enough so that a colored letter, number or figure on the adherent surface can be seen through the finished tape, when said film is the tape backing. In order to obtain sufficient transparency, the films will not contain any substantial amount of the usual opacifying agents, such as titanium dioxide, commonly used in diaper tape film backings. A small amount of a colorant such as a dye or tinting agent may be included in the film if the colorant does not impart noticeable opacity to the film or the tape made therefrom. Generally, an opacity value of less than 0.55 is preferred.

The adhesives used with the transparent films to form the present invention fastening tape may be any of the pressure sensitive adhesives commonly used to provide such adhesive tapes, such as those described in U.S. Pat. No. 3,932,328 (Korpman) or U.S. Pat. No. 3,954,692 (Downey). Any such adhesive which provides a relatively transparent layer is acceptable for the purposes of the present invention. The adhesive can be applied to either the embossed or non embossed face of the film, if only one face is embossed. Further, different adhesive can be used on the end of the fastening tape permanently attached to one side of the closure. This adhesive need not be transparent where the embossed indicia is not displayed, or present, for example on the permanent attachment end of the fastening tape.

Other adjuvants typically added to films, adhesives, or to low adhesion backsizes (LAB's) (which are frequently used on the non-adhesive coated side of an adhesive tape) of the fastening tape, are also required to be used in amounts chosen such that the clarity of the films is not significantly affected. The LAB's themselves must also be transparent. Suitable LAB layers include transparent urethanes or polycarbamates, silicone or siloxane based release agents, fluorocarbons, imides, amides, imines, acrylic polymers or the like.

When numbers, letters and/or various figures are embossed on a clear film, there may be tiny edge lines which define these embossed figures. For the purposes of the present invention, it is considered that such lines do not obscure the transparency or clarity of the embossed films to a significant extent.

The embossed indicia can be, e.g., defined figures or patterns. These figures or patterns can be positively formed by an embossed micropattern or matte surface with, preferably, an unembossed background. Alternatively, any visible figures or patterns can be negatively defined by a continuous embossed background of a micropattern or matte surface. Again, in this latter case preferably the pattern or figure itself would be formed by a relatively smooth (non-embossing) surface on the embossing roll. The figure or pattern would be defined by the background, preferably also with edge lines as discussed above.

The embossing methods described above create a surface having a slight full spectrum haze or opacity. This haze is preferably limited to defined areas which create the described indicium, such as a logo, as a positive or negative image. An unembossed, contrasting surface would provide the greatest image definition. However, the contrasting surface could be lightly embossed with the same or a different pattern as long as the indicia image does not become imperceivable.

The haze formed by the above described embossing techniques is generally over the full visible spectrum. This creates a light or white like diffused color or opacity. When the fastening tape is applied to a surface having a whitish or light color, the color formed by the embossing haze is obscured and the, e.g., embossed surface defined indicia formed as described above, become difficult to visually perceive as shown in FIG. 2. Preferably, for the fastening tape system, the tape landing area, such as a target tape or printed backside portion, having colored indicia, will be predominantly lightly colored or white.

The white color component of the adherent surface or landing area, for the fastening tape, can be described in terms of its L value from the LAB color test (e.g., TAPPI test T-524). Generally, the higher the composite L value of a particular adherent surface, the better its obscuring effect with respect to the embossed formed indicia on the fastening tape. Where it is desired to significantly obscure the fastening tape, embossed surface defined, indicia, while displaying the adherent surface indicia, an adherent surface composite L value of greater than about 50 is preferred, with a value of greater than about 75 being more preferred.

The relative gloss of the adherent surface can have a slight influence on its obscuring effect on the fastening tape embossed defined indicia. Generally, higher gloss substrates are observed to have a slightly lower obscuring effect for embossed defined indicia on a fastening tape. As such, slightly higher L values are preferred for relatively glossy adherent surfaces. However, this effect is relatively negligible for high L value adherent surfaces.

When the substrate to which the invention embossed tape is adhered is darkly colored (e.g., a lower L value), the light or white haze on the fastening tape embossing areas, is more visible. When the fastening tape is placed on such a darkly colored substrate, the positively or negatively embossed formed indicia are more visible. Consequently, where it is desirable to display the embossed defined indicia on a substrate that substrate should be more darkly hued or colored. This may be desirable before the fastening tape free end is applied to the landing area. For example, when the free end of the fastening tape is fixed to a release tape. If it is desired to display a, e.g., logo on the fastening tape free end at this location, the release tape could be darkly dyed or colored. For such a release tape an L value of less than about 40 is preferred, with less than about 30 being more preferred. The, e.g., logo on the fastening tape free end could then be seen both prior to use on the release tape and when being applied and then essentially disappear when on the landing area to display the colored indicia thereon. This could also be done with the permanently adhered end of the fastening tape.

The present invention also relates to transparent logo embossed films, to diapers manufactured using transparent logo embossed films, tapes and to methods for manufacturing such films and diapers.

Although the embossed films and adhesive fastening tape systems of the present invention have been developed and designed for diapers, they will also be useful as fastening systems with other disposable items such as various packaging systems, other disposable garments, adult incontinence devices and the like.

The following, non-limiting examples serve to illustrate the invention, however, are not intended to be limiting thereof. In the following examples, all parts and percentages are by weight unless otherwise indicated.

The following tests are used in the examples and comparative examples for closure evaluation.

SHEAR VALUE

The shear values are determined using modified PSTC-7 as follows. The test substrate to be used is reinforced by laminating to its non-test surface the adhesive layer of a pressure-sensitive adhesive tape having a 0.089 mm thick polypropylene backing (Y-8450 available from 3M Company, St. Paul, Minn.). A fastening tab to be tested is laminated by its adhesive layer to the test surface of the test substrate [1 inch by 1 inch (2.54 by 2.54 cm) test area]. After being allowed to dwell for 15 minutes in an air-circulating oven at 100° F. (38° C.), the bond to the test substrate is tested with a 1000 gram weight attached immediately. The time to fail is recorded, and the test is discontinued if no failure occurs within 1400 minutes. Reported values are averages of multiple tests.

180 DEGREE PEEL VALUE

Tape samples were tested in the following manner. Strips 25 mm wide and 100 mm long were cut from the tape samples. The strips were placed on a 35 micron matte finish polypropylene frontal tape such as is found in Huggies brand disposable diapers (manufactured by Kimberly-Clark) and were rolled down using a 2 kg roller and 2 passes. The tape strips were subsequently peeled at 180 degrees at 305 MM/min peel rates using an Instron Model 1122. The test procedure is that called for in the 180 degree peel adhesion test described in Pressure Sensitive Adhesive Tape Council, PSTC-1.

EXAMPLE 1

A set of diaper tapes was prepared to compare the adhesive properties of tapes of the invention with commercial tapes. Rolls of tapes were prepared using conventional extrusion casting, and coating techniques. Rolls 1 and 2 were embossed with the words "Klean Bebe", rolls 3 and 4 with "3M". The embossing was carried out by casting the extruded polypropylene onto metal rolls which possessed a matte background finish and had further been engraved to give a smooth surface with the desired logo. Each tape was embossed with a selected logo. Each tape was evaluated for 180 degree peel force and shear force as shown in Table II. The following rolls of adhesive diaper tape were prepared:

TABLE I

| ROLL | LOGO | ROLL SIZE | LAB (mg/cm²) | ADHESIVE (mg/cm₂) |
|---|---|---|---|---|
| 1 | Clear "Klean Bebe" | 3" × 140 yd (7.6 cm × 128 mm) | 0.01046* | 2.762** |
| 2 | White "Klean Bebe" | 3" × 140 yd (7.6 cm × 128 mm) | 0.01046* | 2.762** |
| 3 | Clear "3M" | 3" × 140 yd (7.6 cm × 128 mm) | 0.01046* | 2.762** |
| 4 | White "3M" | 3" × 140 yd (7.6 cm × 18 mm) | 0.01046* | 2.762** |

*.025 grains
**6.6 grains

The LAB used was a urethane made by reacting octadecyl isocyanate with a polymer of vinyl alcohol as described in U.S. Pat. No. 2,532,011.

The adhesive used was a tackified styrene-isoprene-styrene block copolymer based adhesive.

The white backings were made by incorporating 2.5 weight percent of titanium dioxide in the backing.

The adhesive properties of the tapes were measured using the test methods described previously and are shown in Table II.

TABLE II

| Roll | Test Method | No. of Reps. | Average |
|---|---|---|---|
| 1 | 180° Peel | 2 | 636 g/2.54 cm |
|   | Shear | 4 | 1400+ minutes |
| 2 | 180° Peel | 2 | 631 g/2.54 cm |
|   | Shear | 4 | 1400+ minutes |
| 3 | 180° Peel | 2 | 667 g/2.54 cm |
|   | Shear | 4 | 1400+ minutes |
| 4 | 180° Peel | 2 | 684 g/2.54 cm |
|   | Shear | 4 | 1400+ minutes |

The tests demonstrate that the adhesive performance of the tapes of the invention is equivalent to the performance of conventional tapes.

EXAMPLE 2

The tape designated roll 1 in Example 1 was tested for its optical performance properties against a number of colored substrates. Each substrate was a colored sheet of paper having the LAB values shown in Table III.

TABLE III

| Substrate | L | A | B | Gloss |
|---|---|---|---|---|
| 1 | 26.71 | 0.71 | −0.6 | 1.8 |
| 2 | 44.6 | 52.45 | 14.27 | 5.3 |
| 3 | 76.41 | −15.9 | 7.4 | 7.2 |
| 4 | 78.20 | 5.41 | −10.41 | 4.5 |
| 5 | 90.20 | −8.5 | 34.7 | 7.2 |
| 6 | 91.7 | 0.4 | 1.4 | 7.2 |
| 7 | 91.7 | −1.1 | 2.5 | 32.1 |

The L value is a measure of whiteness. The higher the L value, the more white the sample. The A value is a measure of green to red, with a negative number indicating green and a positive red. The B value is a measure of blue to yellow, with a negative number indicating blue and a positive number indicating yellow.

The LAB numbers were measured on a Labscan ™ Spectro Colorimeter (Hunter Associates Laboratory, Inc., Reston, Va.) using the TAPPI T-524 procedure.

The gloss number is a 60° gloss measured using a Gardner Instruments (Bethesda, Md.) 60° gloss tester following the procedure outlined in ASTM D2457-70.

The tape was also measured for LAB values according to the procedure outlined above except that 9 tapes were stacked to help eliminate color effects from the tester surface. The LAB values for the tape were: L=78.0, A=−1.7, and B=0.2. Essentially, the tape only had a white component.

The tape was then placed on each of the seven substrates and placed on a wall in a well lighted corridor. The visibility of the logo was examined at 90° from the substrate at distances of approximately one and three feet. The average results (three testers) are shown in Table IV.

TABLE IV

| Sample | ft. | Visible | Slightly Visible | Not Visible |
|---|---|---|---|---|
| 1 | 1 | x |  |  |
|   | 3 | x |  |  |

TABLE IV-continued

| Sample | ft. | Visible | Slightly Visible | Not Visible |
|---|---|---|---|---|
| 2 | 1 | x | | |
|   | 3 | | x | |
| 3 | 1 | | x | |
|   | 3 | | | x |
| 4 | 1 | | x | |
|   | 3 | | | x |
| 5 | 1 | | x | |
|   | 3 | | | x |
| 6 | 1 | | x | |
|   | 3 | | | x |
| 7 | 1 | | | x |
|   | 3 | | | x |

The tape layer was also measured for opacity. The tapes were placed on a PET liner having an opacity of 0.18. 1 to 9 tapes were placed on the PET liner to give adjusted opacity values of 0.23, 0.35, 0.44, 0.52, 0.44, 0.62 and 0.70, respectively. The absolute opacity values were adjusted by subtracting out the opacity value for the PET liner alone. At approximately 4 or 5 tape layers, the images on an adherent surface became significantly obscured. The opacity was measured with a Labscan TM Spectro Colorimeter (Hunter Associates Laboratory, Inc., Reston, Va.) using the TAPPI T-524 procedure.

The various modifications and alterations of this invention will be apparent to those skilled in the art without departing from the scope and spirit of this invention, and this invention should not be restricted to that set forth herein for illustrative purposes.

We claim:

1. A transparent embossed fastening tape for use as a closure in an article comprising a backing layer having opposite faces and an adhesive layer on one face thereof, which layers are transparent to form a transparent tape, the backing layer having means defining embossed indicia on at least one face thereof, which means are obscured by surfaces having an L value of at least 50 when the tape is adhered thereto.

2. The transparent embossed fastening tape of claim 1 wherein the backing layer is a thermoplastic film.

3. The transparent embossed fastening tape of claim 1 wherein the film is formed by casting.

4. The transparent embossed fastening tape of claim 1 wherein the indicia defining means comprises at least one from the group comprising numbers, letters, shapes, patterns or figures negatively defined by an embossed background.

5. The transparent embossed fastening tape of claim 4 wherein the indicia is lightly embossed and appears non-embossed compared to said embossed background.

6. The transparent embossed fastening tape of claim 1 wherein said indicia defining means comprises positively embossed indicia on the backing layer.

7. The transparent embossed fastening tape of claim 1 wherein the embossed indicia defining means comprises an embossed matte surface.

8. The transparent embossed fastening tape of claim 1 wherein the fastening tape further comprises means for attachment to a diaper.

9. The transparent embossed fastening tape of claim 1 wherein the indicia defining means are substantially obscured by an adherent surface having an L value of at least about 75.

10. An adhesive tape fastener for use with a disposable diaper including a liquid impermeable backsheet which backsheet has a front panel portion with printed indicia thereon and a back panel portion, said fastener comprising a substantially transparent adhesive tape fastening means on said back panel portion for interconnecting said back panel portion and said front panel portion, said fastening means having a free end having a region with means defining embossed indicia which are visible on said free end prior to connection to said front panel portion but obscured by said front panel portion while said printed indicia are visible through said free end when said free end is connected to said front panel portion.

11. The fastener of claim 10 wherein said front panel portion comprises a reinforcing tape attached to said liquid impermeable backsheet.

12. The fastener of claim 10 further comprising colored release tape means for releasably attaching to said free end prior to its attachment to the front panel portion which allows display of said embossed indicia defining means.

13. The fastener of claim 10 wherein said back panel portion includes a first corner, said front panel portion includes a second opposing corner and said fastening tape means comprises a first end with means for permanent attachment to said first corner and a second end comprising said free end for attaching to said second opposing corner on said front panel portion having said printed indicia.

14. The fastener of claim 10 wherein the indicia means on said fastener means is obscured by a front panel portion having an L value of at least about 50.

15. The fastener of claim 10 wherein the indicia means on said fastener means is obscured by a front panel portion having an L value of at least about 75.

16. An adhesive closure system for interconnecting indicia surfaces comprising a transparent fastening tape means comprising a transparent film with at least one face with means defining embossed indicia and at least one adherent closure surface having a composite L value of at least about 50, said adherent surface defining a printed indicia surface wherein the embossed indicia defining means on said tape are visible prior to attachment to said closure surface and will display said adherent surface printed indicia therethrough when attached thereto.

17. The adhesive closure system of claim 16 wherein said adherent surface has a composite L value of at least about 75.

* * * * *